United States Patent [19]
Boime

[11] Patent Number: 5,985,611
[45] Date of Patent: Nov. 16, 1999

[54] RECOMBINANT PRODUCTION OF GONADOTROPINS IN SECRETORY CELLS

[75] Inventor: Irving Boime, St. Louis, Mo.

[73] Assignee: Washington University, St. Louis, Mo.

[21] Appl. No.: 07/876,794

[22] Filed: Apr. 30, 1992

[51] Int. Cl.$^6$ .................................................... C12N 15/85
[52] U.S. Cl. ...................... 435/69.4; 435/69.7; 435/325; 530/398
[58] Field of Search .................................. 435/69.7, 69.4, 435/240.2, 172.1, 325; 530/324, 399, 398

[56] References Cited

U.S. PATENT DOCUMENTS 4,828,987  5/1989  Kopchick et al. ......................... 435/68

FOREIGN PATENT DOCUMENTS

WO 90/09800  9/1990  WIPO .

OTHER PUBLICATIONS

Matzuk et al., *Proc. Natl. Acad. Sci.* (1987) 84:6354–6358.
Boothby et al., *J. Biol. Chem.* (1981) 256:5121–5127.
Fiddes et al., *J. Mol. App. Genet.* (1981) 1:3–18.
Fiddes et al., *Nature* (1980) 286:684–687.
Policastro et al., *J. Biol. Chem.* (1983) 258:11492–11499.
Boorstein et al., *Nature* (1982) 300:419–422.
Whitfield et al., "Frontiers in Thyroidology" (1986) Medeiros–Nato et al., Eds., Plenum Press, New York, New York, pp. 173–176.
Watkins et al., *DNA* (1987) 6:205–212.
Jameson, J.L. et al., *Mol. Endocrinol.* (1988) 2:806–815.
Jameson et al., *J. Clin. Endocrinol. Metab.* (1986) 64:319–327.
Glaser et al., *Nature* (1986) 321:882–887.
Maurer et al., *DNA* (1986) 5:363–369.
Kim et al., *DNA* (1988) 7:227–333.
J.G. Hellerman et al PNAS 81:5340–44 1984.
R.N. Clayton et al. Mol. Cell. Endocrinol. 80:193–202 1991.
A.J. Vander et al. "Human Physiology—The Mechanisms of Body Function" McGraw Hill, N.Y. 1975 p. 184.
MA Shupnik et al J. Biol. Chem. 266:17084–17091 1991.
H.J. Steinfelder et al. J. Clin Invest. 89:409–419 Feb. 1989.

*Primary Examiner*—Lorraine Spector
*Attorney, Agent, or Firm*—Morrison & Foerster LLP

[57] ABSTRACT

Improved methods for recombinant production of human reproductive hormones are disclosed. These methods involve the use of animal-derived cells that contain regulated secretory granules as host cells for expression systems capable of expressing DNA encoding human reproductive hormones or their β subunits.

8 Claims, 3 Drawing Sheets

RECOMBINANT PRODUCTION OF GONADOTROPINS IN SECRETORY CELLS

Acknowledgement of Government Support

This invention was made with government support under NIH contract no. NO1-HD-9-2922 awarded by the National Institutes of Health. The U.S. government has certain rights in this invention.

TECHNICAL FIELD

The invention relates to methods for recombinant production of human reproductive hormones with glycosylation patterns more closely related to native patterns than generally obtainable in transformed cells. In particular, it concerns production of recombinant hormones under conditions which result in efficient production and secretion and which regulate the glycosylation pattern of the protein.

BACKGROUND ART

Human reproductive function is controlled in part by a family of heterodimeric human glycoprotein hormones which have a common α subunit, but differ in their hormone-specific β subunits. The family includes follicle-stimulating hormone (FSH), luteinizing hormone (LH), thyrotropin or thyroid-stimulating hormone (TSH), and human chorionic gonadotropin (CG). In all cases, the α subunit is a 92 amino acid glycoprotein with two canonical glycosylation sites at the asparagines located at positions 52 and 78. The β subunits are also glycoproteins; in addition to the N-linked glycosylation exhibited by the β chains of all four hormones, human CG contains four mucin-like O-linked oligosaccharides attached to a carboxy-terminal extension unique to this hormone. The relevance of the O-linked glycosylation is not, apparently, related to the secretion and assembly of the hormone (Matzuk, M. M. et al. *Proc Natl Acad Sci USA* (1987) 84:6354–6358).

Genomic and cDNA clones have been prepared corresponding to the human α chain (Boothby, M. et al. *J Biol Chem* (1981) 256:5121–5127; Fiddes, J. C. et al. *J Mol App Genet* (1981) 1:3–18). The cDNA and/or genomic sequences of the β subunits have also been prepared. For CG, the β-encoding DNA is described by Fiddes, J. C. et al. *Nature* (1980) 286:684–687 and by Policastro, P. et al. *J Biol Chem* (1983) 258:11492–11499. For luteinizing hormone, such description is by Boorstein, W. R. et al. *Nature* (1982) 300:419–422; and for TSH by Hayashizaki, Y. et al. *FEBS Lett* (1985) 188:394–400 and by Whitfield, G. K. et al. in "Frontiers in Thyroidology", (1986) Medeiros-Nato, G. et al. (eds) pages 173–176, Plenum Press, N.Y. These DNA segments have been expressed recombinantly, and biologically active material has been produced.

The genomic sequence encoding FSH-β chain was used to construct a recombinant expression vector containing the complete β chain coding sequence as described in PCT application WO 86/04589, published Aug. 14, 1986. In addition genomic clones for human FSH-β have been prepared by others (Watkins, P. C. et al. *DNA* (1987) 6:205–212; Jameson, J. L. et al., *Mol Endocrinol* (1988) 2:806–815; Jameson, J. L. et al. *J Clin Endocrinol Metab* (1986) 64:319–327; Glaser, T. et al. *Nature* (1986) 321:882–887). PCT application WO 90/09800 describes the expression of human FSH in Chinese hamster ovary cells. The bovine β-FSH gene has also been obtained as disclosed in Maurer, R. A. et al. *DNA* (1986) 5:363–369; Kim, K. E. et al. *DNA* (1988) 7:227–333.

The above-referenced PCT application WO 90/09800 discloses a number of expression systems for human reproductive hormones including their α subunits and β subunits. In addition, this application describes certain muteins of the α and β subunit that are useful by virtue of their alteration of secretion characteristics or glycosylation patterns. However, the expression systems described specifically in the above-referenced PCT application are limited to murine cells and Chinese hamster ovary cells. The present application describes the use of expression systems of the type disclosed in the above-referenced application in cells containing secretory granules, especially pituitary-derived cells, thus resulting in mature forms of the β subunits or hormone dimers and an enhanced capability of the cells to secrete the hormone.

DISCLOSURE OF THE INVENTION

The invention provides cultures which are capable of secreting forms of human reproductive hormones, including their individual β subunits, and including muteins of the hormones and subunits which have glycosylation patterns similar to the natively produced materials and which are capable of being secreted into the medium. Secretion into the medium greatly eases the process of purification of the hormone produced and the glycosylation mimicking that of the native substance permits better predictability of behavior in vivo in view of the accumulation of data with regard to the native materials.

Thus, in one aspect, the invention is directed to a method to produce human reproductive hormones or their β subunits recombinantly, which method comprises culturing cells derived from animal tissue which cells contain secretory granules, that have been transformed with an expression vector capable of expressing a DNA encoding said human reproductive hormone or β subunit thereof under conditions where said expression is effected and recovering the hormone or subunit from the supernatant of the culture. In another aspect, the invention is directed to the cultures of these transformed cells useful in the method of the invention.

MODES OF CARRYING OUT THE INVENTION

Figure 1:
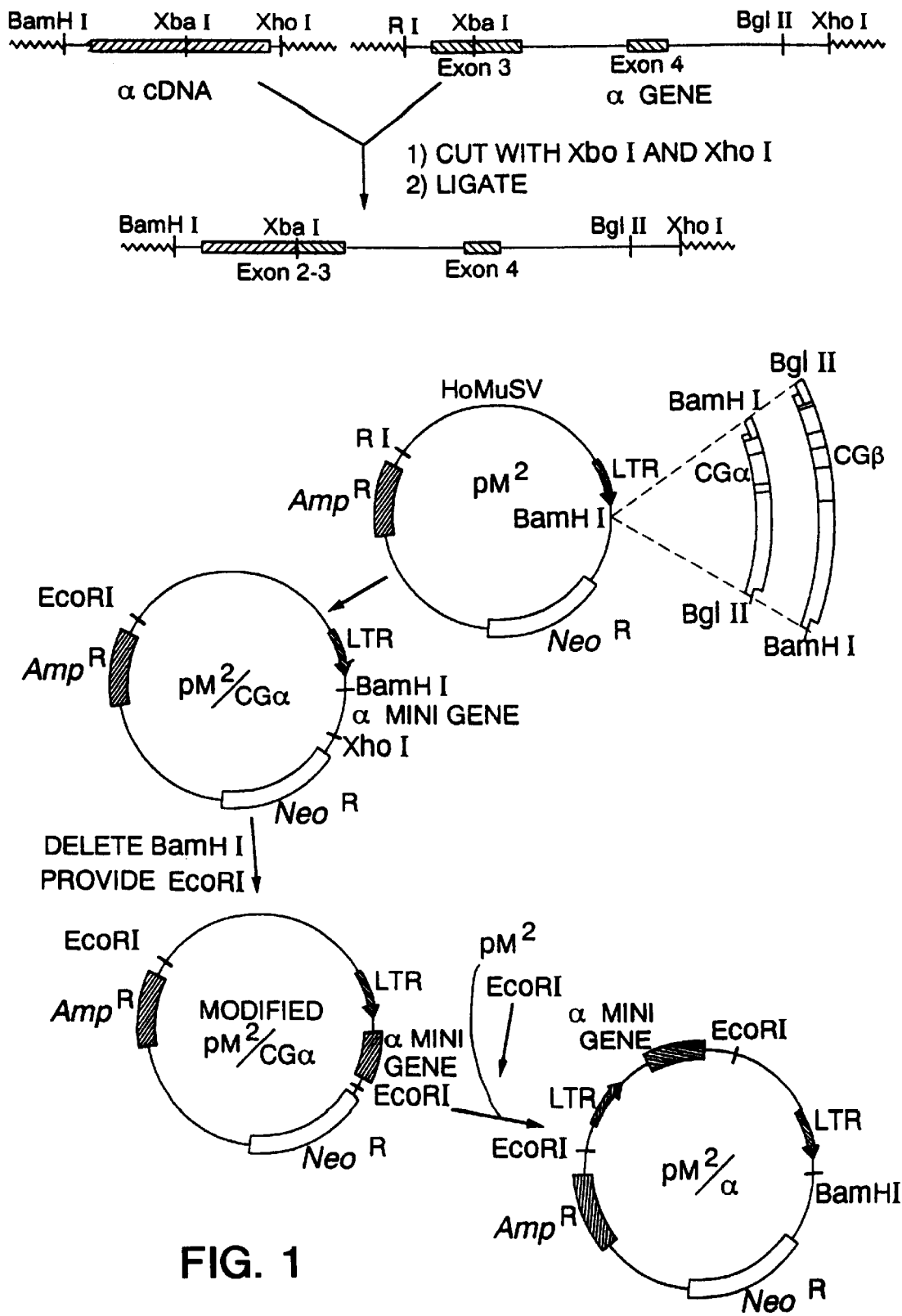
FIG. 1 shows the construction of the human α subunit minigene, and vectors for its expression.

As used herein, human α subunit, and human FSH, LH, TSH, and CGβ subunits as well as the heterodimeric forms have in general their conventional definitions and refer to the proteins having the amino acid sequences known in the art per se, or allelic variants thereof, deliberately constructed muteins thereof maintaining the activity of the native protein regardless of the glycosylation pattern exhibited, or mutant forms thereof having at least 90% homology with the native forms. "Human reproductive hormones" or, alternatively, "human gonadotropins" refers to these four heterodimers (or their muteins).

"Native" forms of these hormones or subunits are those which have the amino acid sequences isolated from human tissue, and have these known sequences per se, or their allelic variants.

"Mutein" forms of these proteins are those which have deliberate alterations in amino acid sequence produced by, for example, site-specific mutagenesis or by other recombinant manipulations, or which are prepared synthetically. These alterations result in amino acid sequences wherein the biological activity of the subunit is retained and/or wherein the subunit has at least 90% homology with the native form.

For example, a preferred mutein of the α subunit for use in antagonists of the various heterodimers has alterations in the amino acids of positions 88–92.

A particularly preferred mutein of FSH-β or LH-β, for example, is an "extended" FSH-β or LH-β wherein the amino acid sequence comprising the carboxy terminal peptide (CTP) of hCG is fused to the carboxy terminus of FSH-β or LH-β. As used herein, "CTP" refers to the "extra" sequence at the C-terminus of the CG-β peptide as compared to the other related hormones. The length of the effective CTP as compared to the other β subunits may vary slightly but it extends from roughly amino acid 112–118 of CG to residue 145 at the C-terminus. The precise length of CTP in the constructs herein will be clear from the content.

In the fusions described herein, native CTP can be used or a "variant" thereof. By "variant" is meant a conservative analog of the peptide residues from about 112–118 to 145, i.e. this sequence wherein about 1–5 amino acids of the sequence are altered without substantial change in properties. Often this variation results simply from mutation to obtain appropriate restriction sites.

Although it is recognized that glycosylation pattern has a profound influence on activity both qualitatively and quantitatively, for convenience the terms FSH, LH, TSH, and CG β subunits refers to the amino acid sequence characteristic of the peptides, as does "α subunit". When only the β chain is referred to, the terms will be, for example, FSH-β; when the heterodimer is referred to, the simple term "FSH" will be used. It will be clear from the context in what manner the glycosylation pattern is affected by, for example, recombinant expression host or alteration in the glycosylation sites. Forms of the glycoprotein with specified glycosylation patterns will be so noted.

As used herein, the a subunit "minigene" refers to the gene construction disclosed in PCT application WO 90/09800 in the description of the construction of pM$^2$/CGα or pM$^2$/α. This "minigene" is characterized by retention only of the intron sequence between exon III and exon IV, all upstream introns having been deleted. In the particular construction described, the N-terminal coding sequences which are derived from exon II and a portion of exon III are supplied from cDNA and are ligated directly through an XbaI restriction site into the coding sequence of exon III so that the introns between exons I and II and between exons II and III are absent. However, the intron between exons III and IV as well as the signals 3' of the coding sequence are retained. The resulting minigene can conveniently be inserted as a BamHI/BglII segment. Other means for construction of a comparable minigene are, of course, possible and the definition is not restricted to the particular construction wherein the coding sequences are ligated through an XbaI site. However, this is a convenient means for the construction of the gene, and there is no particular advantage to other approaches, such as synthetic or partially synthetic preparation of the gene. The definition includes those coding sequences for the α subunit which retain the intron between exons III and IV but no other introns.

A "transformed" recombinant host cell, i.e., a cell "transformed" with the recombinant expression systems of the invention, refers to a host cell which has been altered to contain this expression system by any convenient manner of introducing it, including transfection, viral infection, and so forth. "Transformed" refers to cells containing this expression system whether the system is integrated into the chromosome or is extrachromosomal. The "transformed" cells may either be stable with respect to inclusion of the expression system or not. In short, recombinant host cells "transformed" with the expression system of the invention refers to cells which include this expression system as a result of their manipulation to include it, when they natively do not, regardless of the manner of effecting this incorporation.

"Expression system" refers to a DNA sequence which includes a coding sequence to be expressed and those accompanying control DNA sequences necessary to effect the expression of the coding sequence. Typically, these controls include a promoter, termination regulating sequences, and, in some cases, an operator or other mechanism to regulate expression. The control sequences are those which are designed to be functional in a particular target recombinant host cell and therefore the host cell must be chosen so as to be compatible with the control sequences in the constructed expression system.

As used herein "cells", "cell cultures", and "cell lines" are used interchangeably without particular attention to nuances of meaning. Where the distinction between them is important, it will be clear from the context. Where any can be meant, all are intended to be included.

Certain cells are known to contain dense-core secretory granules and to secrete proteins through a regulated pathway, which can be stimulated by certain substances, for example, forskolin. These cells or cell lines, derived from appropriate animal tissues, are the host cells of the invention. Included among such cells are cells of the secretory components of the hormone system such as the pituitary, β islet cells, and cells of the adrenal cortex. Particularly preferred in the method of the invention are pituitary-derived cells.

Consistent with the foregoing paragraph, "cells derived from pituitary" refers the cells or cell lines which are cultured from pituitary tissue derived from animal species, in particular mammalian species, and more particularly, human or murine pituitaries. Illustrated herein is the GH$_3$ murine cell line described by Tasjian, J., *Methods Enzymol* (1979) 58:527. However, other lines derived from the pituitary are also known and obtainable from public depositories. In addition, cells derived directly from pituitaries may be used.

Cells containing regulated secretory granules provide glycosylation patterns to proteins to be secreted which permits them to be targeted to the regulated secretory pathway. Production of the reproductive hormones in such cells, containing dense-core secretory granules capable of secreting proteins through a regulated pathway thus results in the production of secreted forms of these materials with glycosylation patterns similar to those found in the native hormones or subunits. In particular, these forms of the hormones or subunits such as LH which retain labeled sulfur supplied in the form of sulfate do so when produced in these cells indicating that sulfated glycosylation units are present in these forms. Labeled $SO_4^{-2}$ is not incorporated into LH produced in CHO cells or murine C127 cells.

Expression Vectors

To construct suitable expression vectors for use in the secretory cells of the invention, a convenient construct, illustrated for the α subunit minigene is reproduced from the above-referenced PCT application as FIG. 1. As shown in this figure, and as more fully explained in the above-referenced application, the sequence encoding the α subunit is prepared as a minigene wherein the portions of the peptide encoded by exons II–III are fused but separated from exon IV. This construct is ligated into the host vector pM$^2$ under the control of the long terminal repeat shown in FIG. 1 to obtain pM$^2$/CGα or to obtain pM$^2$α which contains an additional insertion site for another coding DNA. As further shown in FIG. 1, the BamHI site contained in the host vector pM$^2$ can be used to accommodate the β subunits of the human reproductive proteins for expression of these subunits per se, as the BamHI site under control of the LTR is available in pM$^2$/α.

Thus, the β subunits per se may be produced by ligating the coding DNA into pM$^2$ as shown, or the heterodimer may be produced by cotransformation of pM$^2$ containing DNA encoding β subunit with pM$^2$/CGα. The heterodimer may also be produced from the single vector wherein the β insert is ligated into the above-mentioned BamHI site of pM$^2$/α.

The foregoing constructions are, of course, merely illustrative of expression vectors or systems which can be constructed for the production of α subunits or the corresponding heterodimeric hormones. Alternate control sequences including, for example, different promoters, can be ligated to the coding sequence of human β subunits or the α minigene to effect expression. A variety of control sequences is known in the art, and methods to ligate the β subunits or α minigene coding sequence (or other α-encoding construct) are of course also available. Suitable mammalian promoters include the early and late promoters from SV40, or other viral promoters such as those derived from polyoma, adenovirus 2, bovine papilloma virus or avian sarcoma viruses. Suitable viral and mammalian enhancers can also be used.

As set forth in the Background section above, the recovery of the genes for the various human reproductive hormones, including their β subunits, has already been described. The genes can be recovered from native sources as described in the art, or the genes can be entirely or partially synthesized using standard solid phase oligonucleotide synthesis techniques as described, for example, by Nambiar, K. P. et al. *Science* (1984) 223:1299 or by Jaye, E. et al. *J Biol Chem* (1984) 259:6311. These techniques are now commercially available. It is evident, of course, that not only the specific native nucleotide sequences can be employed, but also nucleotide sequences employing codons which are degenerate with these, as well as allelic forms.

Figure 2:
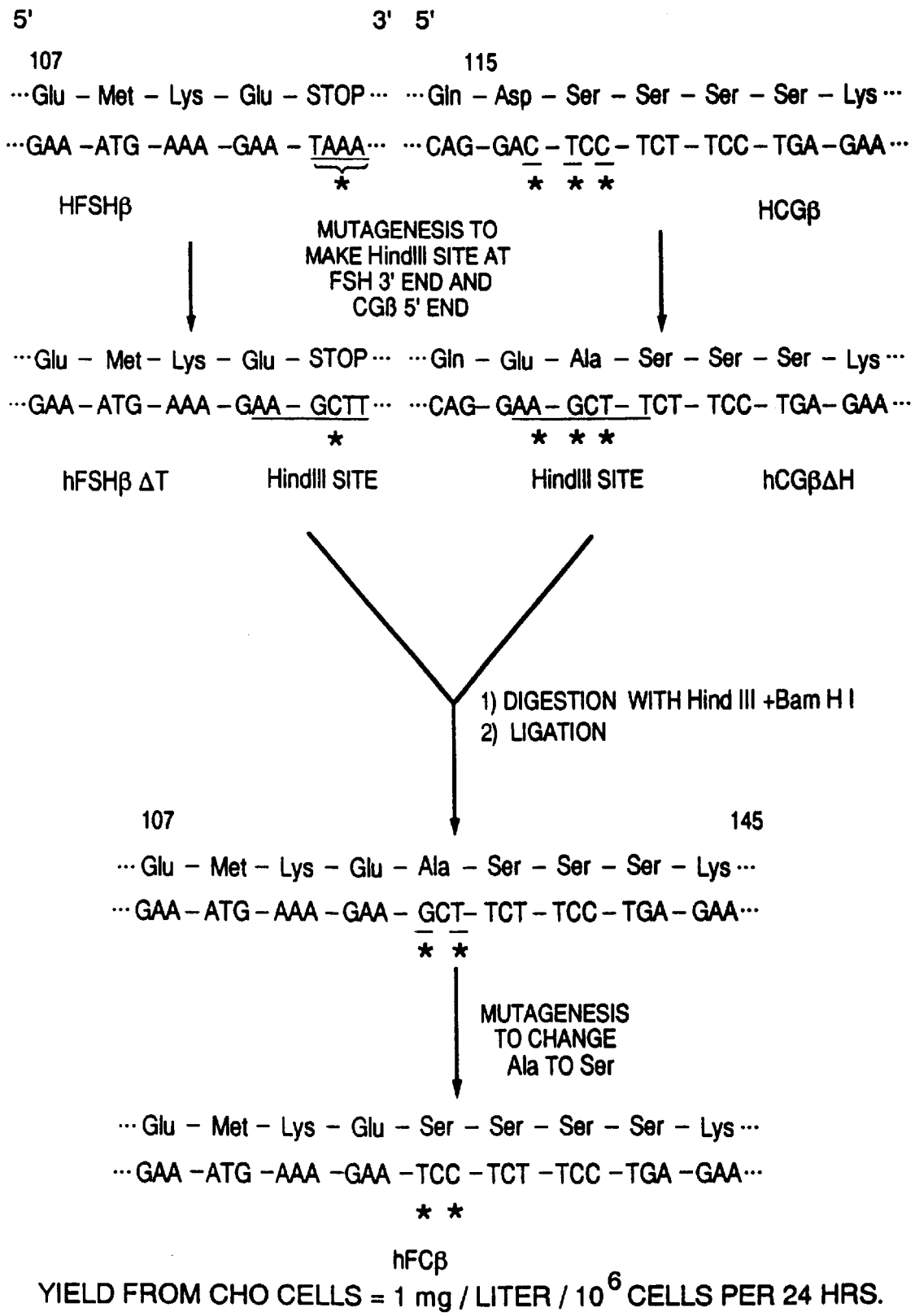
FIG. 2 shows the construction of the extended form of FSH β subunit.

As further described in the above-referenced PCT application, muteins of the various hormones can be obtained which have agonist or antagonist activity. These mutein-encoding genes may be inserted into the relevant host vectors in a manner similar to that described for the native forms. Of particular interest are muteins wherein the β subunits of LH, TSH or FSH are extended by the carboxy terminal peptide native to chorionic gonadotropin. One such construct is illustrated in FIG. 2 for human FSH. In addition, as further described in U.S. application Ser. No. 07/771,262, filed Oct. 4, 1991, and incorporated herein by reference, more than one of the CTP units may be used to extend the β chains.

Transformation and Cell Culture

In general, the selected expression vector or vectors is transfected or otherwise transformed into the host cells of the invention using procedures similar to those used generally for mammalian cells. The techniques for transformation are substantially those applied with respect to Chinese hamster ovary cells, and systems for markers for selection of successful transformants are also substantially identical. Cell culture conditions for the transformed cells may be modified as is generally understood to accommodate the particular needs of the selected host cell line which will contain regulated secretory granules; however, culture conditions are substantially similar to those used for CHO cells as well.

In an illustrative approach to transfection and culture, the β subunit-encoding gene is inserted into pM$^2$ and then transfected alone or along with pM$^2$/CGα into the cells appropriate for the method of the invention which contain regulated secretory granules or into Chinese hamster ovary cells as a control, as described by Matzuk, M. M., et al., *Proc Natl Acad Sci USA* (1987) 84:6354–6358; Matzuk, M. M., et al., *J Cell Biol* (1988) 106:1049–1059. Successful transformants are selected in 0.25 ug/ml G418, and expression may be detected by immunoprecipitation of metabolically labeled cells to select monomer- and dimer-secreting cell lines.

Both stably transfected hosts containing regulated secretory granules and stably transfected CHO cell lines are maintained in "medium-1" (Ham's F12 medium supplemented with penicillin (100 U/ml), streptomycin (100 µg/ml), and glutamine (2 mM)) containing 5% of v/v fetal calf serum on 0.125 mg/ml G418 in a humidified 5% CO$_2$ incubator.

Labeling

Both cells of the invention and CHO cells are plated at 300,000–350,000 cells per well into 12-well dishes in 1 ml medium 1 supplemented with 5% fetal calf serum 1 day prior to labeling. For continuous labeling, cells are washed twice with cysteine-free "medium-2" (medium-1 supplemented with 5% dialyzed calf serum) and labeled for 6 hours in 1 ml of cysteine-free medium 2 containing 20 uCi/ml labeled cysteine. For pulse chase experiments, the cells are washed twice and preincubated for 1.5 hours in cysteine-free medium-2, followed by a 20 minute labeling in cysteine-free medium-2 containing 100 uCi/ml labeled cysteine, then washed twice with medium 2 containing 1 mM unlabeled cysteine and incubated in the unlabeled medium.

Labeling experiments using incorporation of 35S-labeled sulfate are conducted similarly in more detail.

The medium and cell lysates are prepared, immunoprecipitated, and treated as described by Corless, C. L., et al., *J Cell Biol* (1987) 104:1173–1181, and in the Matzuk *PNAS* paper cited above. Antisera against CG-β, LH-β, FSH-β and TSH-β and the α subunit are prepared by standard methods; antisera generated against CG-β cross-reacts fully with LH-β and was used to detect LH-β as well. For characterization of the immunoprecipitates on SDS gels, 15% SDS polyacrylamide gels were soaked for 10 minutes in 1 M sodium salicylate, dried, and autoradiographed with preflash film, and scanned, if desired, with an LKB Ultrascan XL laser densitometer.

As a control, the results of production of human FSH in CHO cells as assessed by labeling with cysteine is reproduced here. The expression systems described above for human FSH-β inserted into pM$^2$ for expression of FSH-β alone or into pM$^2$/α for expression in tandem with the α subunit were transfected into CHO cells and stable clones shown to express the β subunit or dimer were continuously labeled with $^{35}$S-cysteine for 6 hr. Yields of secreted FSH of approximately 1 mg/10$^6$ cells/24 hr cultured in 1 L of medium are obtained.

The proteins secreted into the media and from cell lysates were immunoprecipitated with appropriate antisera and resolved on SDS-PAGE. The results were compared to the behavior of similar transformants expressing the gene for human CG-β.

Gels from 6 hr labeling show that in the absence of the α subunit, FSH-β is retained in the lysate. When the α subunit is present, the dimer is formed and efficiently secreted into the medium. The results of experiments wherein the cells are pulse labeled with 35-S cysteine for 20 min. and chased with cysteine for up to 12 hr show that the β subunit of CG has a lower molecular weight when secreted into the medium, apparently due to the differences in the extent of glycosylation at the two Asn-linked glycosylation sites on CG-β and unique to this β subunit. The half-life of CGβ from lysates and appearance of CG-β in the medium are identical at about 2 hr and almost all the secreted β subunit can be recovered.

FSH-β alone is secreted much less efficiently and, as does CG-β, disappears from the cell lysates after about 5 hr; less than 20% is recovered in the medium after 12 hr. Similarly to the β subunits of LH and TSH, FSH-β alone is inefficiently secreted and slowly degraded intracellularly. However, the presence of the α subunit stabilizes and enhances the secretion of the β subunit for FSH. The half-life of disappearance from the lysates was about 90 min, and 90% was recovered in the medium after 12 hr. This behavior is similar to that shown for TSH above, but different from both CG and LH.

It is apparent from the foregoing results that difficulties with secretion are experienced for expression in CHO cells of the genes encoding the β subunits alone; in some instances, this secretion ability is mitigated by the presence of a vector encoding the α subunit. However, in general, it appears that CHO cells are not efficient secretors of the desired β subunits or corresponding human reproductive hormones.

Another difficulty which is apparent from experiments using sulfate label as a source of 35S is that for LH-β subunit or the LH heterodimer, which is known to contain sulfated glycosylation in its native state, incorporation of label does not take place in CHO cells. Thus, at least for LH, and for the α portion of the heterodimer, which also contains sulfated glycosylation, CHO cells are unable to reproduce the native pattern for glycosylation. Thus, it has been shown that using, in place of cysteine, labeled sulfate as a source of radioactivity, label does not appear in the dimer or the β subunit of LH produced in CHO cells.

Expression in Pituitary Cells

The expression vectors described above including the β subunits for LH-β, CG-β or FSH-β either with or without the α subunit, and with the α subunit encoded on the same or different vector were transformed into the rat pituitary cell line $GH_3$. After steady state labeling by either sulfate (for LH) or cysteine-originated (for all forms) S35, mature forms of LH, FSH and hCG which contained processed oligosaccharides were stored in the cells and their release was stimulated by forskolin. The majority of the β subunits of these hormones appeared to be Endo H sensitive and thus reside in the ER, but the Endo H resistant fraction, which is the mature form, was targeted to the regulatory secretory pathway with an efficiency that was comparable between the dimer and the β subunit.

Figure 3:
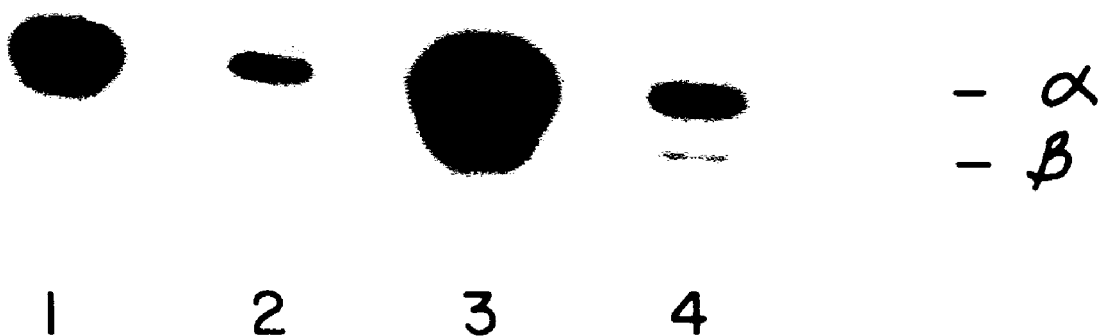
FIG. 3 shows 35-S cysteine labeled LH-α subunit and 35-SO$_4$ labeled or 35-S-cysteine labeled LH dimer recombinant supernatants.

FIG. 3 shows the results obtained from $GH_3$ cells which have been transformed with $pM^2/α$ into which the coding sequence for LH-β subunit has been inserted into the alternate BamHI site. Lanes 1 and 2 are controls from $GH_3$ cells which are transformed only by $pM^2/CGα$; as is evident from the results, the α subunit is found mostly in the cells themselves lane 1 rather than in the supernate lane 2. On the other hand, lanes 3 and 4 represent the results obtained by immunoprecipitating the heterodimer labeled as described above using cysteine or sulfate and assaying the cell medium. As seen from these results, a large amount of the heterodimer is secreted into the medium and both the α and β subunit are able to take up label from S35 sulfate.

Assembly of the β subunits of these hormones and secretion of the dimers is increased many-fold over that seen in CHO cells. The oligosaccharide in the LH dimer is also sulfated; however, FSH is normally sialylated in vivo, and thus does not take up label from $SO_4$.

It has been demonstrated that complete deglycosylation of human chorionic gonadotropin results in a hormone which retains its ability to bind to receptor, but is no longer capable of effecting the ordinary biological response of the cell on which the receptor is borne. Similar effects of complete deglycosylation are obtained with the additional reproductive hormones LH and FSH. Accordingly, alteration of the glycosylation pattern in the β subunits may result in alternative properties. The glycosylation of the hormones and subunits produced by the method of the invention, however, more closely resembles that of the native forms.

Utility and Administration

The hormones and other pharmaceuticals of the present invention are formulated for administration using methods generally understood in the art. Typical formulations and modes of administration are described in *Remington's Pharmaceutical Sciences*, Mack Publishing Co., Easton, Pa., latest edition. These formulations are typically for systemic administration, such as by injection, but oral formulations or topical formulations may also be employed.

The choice of formulation, mode of administration, and dosage level are dependent on the particular hormone or protein and can be optimized for the appropriate indication using generally recognized techniques.

I claim:

1. An improved method for recombinant production of a human gonadotropin, which method comprises culturing animal cells that contain regulated secretory granules and which cells have been transformed with an expression system said expression system comprising nucleotide sequences encoding said gonadotropin operably linked to sequences that control expression and secretion under conditions wherein said encoding nucleotide sequences are expressed, and said gonadotropin is secreted; and recovering the gonadotropin from the culture medium.

2. The method of claim 1 wherein said cells are pituitary cells.

3. The method of claim 2 wherein said pituitary cells are $GH_3$ cells.

4. The method of claim 1 wherein the gonadotropin is FSH or LH.

5. A cell culture which secretes a human gonadotropin which cell culture comprises animal cells that contain regulated secretory granules and which cells have been transformed with an expression system said expression system comprising nucleotide sequences encoding said gonadotropin operably linked to sequences that control expression and secretion.

6. The culture of claim 5 wherein said cells are pituitary cells.

7. The culture of claim 6 wherein said pituitary cells are $GH_3$ cells.

8. The culture of claim 5 wherein the gonadotropin is FSH or LH.

* * * * *